(12) United States Patent
Barrat et al.

(10) Patent No.: US 7,122,340 B2
(45) Date of Patent: *Oct. 17, 2006

(54) REGULATORY T CELLS; METHODS

(75) Inventors: Franck J. Barrat, San Mateo, CA (US); Pieter Andre Boonstra, San Francisco, CA (US); Huub Savelkoul, Bennekom (NL); Rene de Waal Malefyt, Sunnyvale, CA (US); Anne O'Garra, Palo Alto, CA (US)

(73) Assignee: Schering Corporation, Kenilworth, NJ (US)

( * ) Notice: Subject to any disclaimer, the term of this patent is extended or adjusted under 35 U.S.C. 154(b) by 169 days.

This patent is subject to a terminal disclaimer.

(21) Appl. No.: 10/685,323

(22) Filed: Oct. 14, 2003

(65) Prior Publication Data

US 2004/0087018 A1 May 6, 2004

Related U.S. Application Data

(62) Division of application No. 09/970,446, filed on Oct. 3, 2001, now Pat. No. 6,670,146.

(60) Provisional application No. 60/239,023, filed on Oct. 4, 2000.

(51) Int. Cl.
*C12P 1/00* (2006.01)
*C12N 5/00* (2006.01)
*C12N 5/02* (2006.01)

(52) U.S. Cl. ............ 435/41; 435/325; 435/383; 435/377; 435/405

(58) Field of Classification Search ............ 435/41, 435/325, 383, 375, 377, 405
See application file for complete search history.

(56) References Cited

U.S. PATENT DOCUMENTS 5,858,358 A * 1/1999 June et al. ............ 424/130.1
6,670,146 B1 * 12/2003 Barrat et al. ............ 435/41

FOREIGN PATENT DOCUMENTS

WO   WO 91/04030   4/1991

OTHER PUBLICATIONS

M. Heloisa Blotta, et al., *J Immunol*, 158(12):5589-5595, Jun. 15, 1997. "Corticosteroids inhibit IL-12 production in human monocytes and enhance their capacity to induce IL-4 synthesis in CD4+ lymphocytes".

Frank Bridoux, et al., *J Exp Med*, 185(10):1769-1775, May 19, 1997. "Transforming growth factor beta (TGF-beta)-dependent inhibition of T helper cell 2 (Th2)-induced autoimmunity by self-major histocompatibility complex (MHC) class II-specific, regulatory CD4(+) T cell lines".

Jan Buer, et al., *J Exp Med*, 187(2):177-183, Jan. 19, 1998. "Interleukin 10 secretion and impaired effector function of major histocompatibility complex class II-restricted T cells anergized in vivo".

Nitya G. Chakraborty, et al., *J Immunol*, 162(9):5576-5583, May 1, 1999. "Emergence of regulatory CD4+ T cell response to repetitive stimulation with antigen-presenting cells in vitro: implications in designing antigen-presenting cell-based tumor vaccines".

Rongbing Chen, et al., *J Immunol*, 164(2):825-832, Jan. 15, 2000. Glucocorticoids inhibit calcium- and calcineurin-dependent activation of the human IL-4 promoter.

Daniele D'Ambrosio, et al., *J Clin Invest*, 101(1):252-262, Jan. 1, 1998. "Inhibition of IL-12 production by 1,25-dihydroxyvitamin D3. Involvement of NF-kappaB downregulation in transcriptional repression of the p. 40 gene".

Karolien De Bosscher, et al., *Proc Natl Acad Sci U S A*, 94(25):13504-13509, Dec. 9, 1997. "Glucocorticoid-mediated repression of nuclear factor-kappaB-dependent transcription involves direct interference with transactivation".

Herve Groux, et al., *Nature*, 389(6652):737-742, Oct. 16, 1997. "A CD4+ T-cell subset inhibits antigen-specific T-cell responses and prevents colitis".

Giandomenica Iezzi, et al., *Eur J Immunol*, 29(12):4092-4101, Dec. 1999. "The interplay between the duration of TCR and cytokine signaling determines T cell polarization".

Michael Karin, *Cell*, 93(4):487-490, May 15, 1998. "New twists in gene regulation by glucocorticoid receptor: is DNA binding dispensable?".

Ui Yen Khoo, et al., *J Immunol*, 158(8):3626-3634, Apr. 15, 1997. CD4+ T cell down-regulation in human intestinal mucosa: evidence for intestinal tolerance to luminal bacterial antigens.

Frank Mattner, et al., *Eur J Immunol*, 30(2):498-508, Feb. 2000. "Inhibition of Th1 development and treatment of chronic-relapsing experimental allergic encephalomyelitis by a non-hypercalcemic analogue of 1,25-dihydroxyvitamin D(3)".

Carla Miller, et al., *J Exp Med*, 190(1):53-64, Jul. 5, 1999. "Anergy and cytokine-mediated suppression as distinct superantigen-induced tolerance mechanisms in vivo".

Anne O'Garra, *Immunity*, 8(3):275-283, Mar. 1998. "Cytokines induce the development of functionally heterogeneous T helper cell subsets".

(Continued)

*Primary Examiner*—Christina Chan
*Assistant Examiner*—Michail Belyavskyi
(74) *Attorney, Agent, or Firm*—Edwin P. Ching; Sheela Mohan-Peterson

(57) ABSTRACT

Methods for increasing yields of regulatory T cells, useful, e.g., in transplantation contexts. Use of antigen presenting cells and anti-CD28 are also described.

9 Claims, No Drawings

OTHER PUBLICATIONS

Lorenzo Piemonti, et al., *J Immunol*, 164(9):4443-4451, May 1, 2000. "Vitamin D3 affects differentiation, maturation, and function of human monocyte-derived dendritic cells".

Francisco Ramirez, et al., *J Immunol*, 156(7):2406-2412, Apr. 1, 1996. "Glucocorticoids promote a TH2 cytokine response by CD4+ T cells in vitro".

David F. Richards, et al., *Eur J Immunol*, 30(8):2344-2354, Aug. 2000. "Glucocorticoids drive human CD8(+) T cell differentiation towards a phenotype with high IL-10 and reduced IL-4, IL-5 and IL-13 production".

Chao-Zhong Song, et al., *Proc Natl Acad Sci U S A*, 96(21):11776-11781, Oct. 12, 1999. "Glucocorticoid receptor inhibits transforming growth factor-beta signaling by directly targeting the transcriptional activation function of Smad3".

Pedro L. Vieira, et al., *J Immunol*, 161(10):5245-5251, Nov. 15, 1998. "Glucocorticoids inhibit bioactive IL-12p70 production by in vitro-generated human dendritic cells without affecting their T cell stimulatory potential".

Jeroen Visser, et al., *Blood*, 91(11):4255-4264, Jun. 1, 1998. "Differential regulation of interleukin-10 (IL-10) and IL-12 by glucocorticoids in vitro".

Thomas Wilckens and Roel De Rijk, *Immunol Today*, 18(9):418-424, Sep. 1997. "Glucocorticoids and immune function: unknown dimensions and new frontiers".

Junn Yanagisawa, et al., *Science*, 283(5406):1317-1321, Feb. 26, 1999. "Convergence of transforming growth factor-beta and vitamin D signaling pathways on SMAD transcriptional coactivators".

* cited by examiner ated application Ser. No. 09/970,446, filed Oct. 3, 2001, now U.S. Pat. No. 6,670,146, which claims benefit of U.S. provisional patent application 60/239,023, filed Oct. 4, 2000, each of which is incorporated by reference.

REGULATORY T CELLS; METHODS

This filing is a divisional of commonly assigned application Ser. No. 09/970,446, filed Oct. 3, 2001, now U.S. Pat. No. 6,670,146, which claims benefit of U.S. provisional patent application 60/239,023, filed Oct. 4, 2000, each of which is incorporated by reference.

FIELD OF THE INVENTION

The invention relates generally to methods of preparing immune cells in a mammal. These cells, designated regulatory T cells, produce IL-10 and can suppress antigen specific immune responses.

BACKGROUND

Interleukin-10 is a cytokine which was originally characterized by its activities in suppressing production of Th1 cytokines. See, e.g., de Vries and de Waal Malefyt (eds. 1995) Interleukin-10 Landes Co., Austin, Tex.; and Fowler and Powrie (1999) *Springer Semin. Immunopathol.* 21(3): 287–294. Th1 cells are implicated in the induction of pathology in transplantation and autoimmune contexts.

Suppression of immunological function finds utility in many different contexts. See, e.g., Paul (ed. 1998) *Fundamental Immunology* 4th ed., Raven Press, NY. In particular, allogeneic immunity is important in a transplantation context, due largely to its extraordinary strength. As organ and tissue transplants become more common in medical contexts, the ability to minimize problems from tissue rejection exhibit larger economic advantages. In addition, means to minimize adverse autoimmune conditions, to block certain responses to particulate antigens, e.g., bacterial and parasitic, and to minimize the reaction to certain soluble antigens, both protein and allergens, will be significant advances for therapeutic purposes.

The lack of fully effective therapeutics to minimize or eliminate tissue rejection, graft vs. host disease, autoimmunity, or these other immunological responses leads to many problems. The present invention addresses and provides solutions to many of these problems.

SUMMARY OF THE INVENTION

The present invention is based, in part, upon the surprising discovery of methods to improve the efficiency, yield, and/or purity of regulatory T cell populations.

The present invention provides methods comprising contacting a naive T cell with a stimulatory signal and an appropriate amount of a combination of Vitamin D3 and Dexamethasone, wherein the contacting results in differentiation to a regulatory T cell. In certain embodiments, the regulatory T cell produces essentially only the cytokine IL-10; stimulatory signal is activation with an antigen or anti-CD3, e.g., where stimulation is with: antigen, e.g., HLA, and antigen presenting cells; or anti-CD3 and anti-CD28. Particularly, the contacting may be in vitro, and/or repeated two times. Typically, the amount of Vitamin D3 is about 4 times as much as Dexamethasone, and may be at least $10^{-9}$ M; and/or at least $4 \times 10^{-9}$ M, respectively, and preferably at least $4 \times 10^{-8}$ M; and/or at least $10^{-8}$ M, respectively.

In other embodiments, the regulatory cell suppresses the response to a defined antigen; or the contacting occurs in the presence of an antagonist of IL-4, of IFN-γ, and/or IL-12. For example, the response may be a pathology inducing response; or the contacting may occur in the presence of at least two of the antagonists. Typically, the regulatory T cells produce: at least 100 ng of IL-10 per $10^6$ cells; less than 1 ng of IL-4 per $10^6$ cells; less than 30 pg IL-5 per $10^6$ cells; and/or less than 30 pg IFN-γ per $10^6$ cells. The invention also provides populations of cells made by the described methods.

Further methods include those which further comprise administering the regulatory T cell to an animal with specific antigen. Preferably, the regulatory T cell and the antigen are administered simultaneously; the animal exhibits signs or symptoms of an inflammatory or autoimmune pathology; or the administering results in suppression of an inflammatory or autoimmune pathology.

Yet other methods are provided, e.g., comprising administering regulatory T cells specific for an exogenous antigen with the antigen to an animal undergoing an inflammatory or autoimmune pathology. In some embodiments: the exogenous antigen is ovalbumin; or the regulatory T cells and antigen are administered simultaneously. Preferably, the administering results in suppression of the pathology.

DETAILED DESCRIPTION OF THE INVENTION

Outline

I. General

II. Regulatory T Cells
   A. Vitamin D and Dexamethasone
   B. Properties

III. Uses

I. General

T-regulatory cells have an important role in peripheral tolerance, but it has been difficult to isolate a homogeneous population of cells with suppressive activity in vitro and to define their mechanism of action. A CD4+ T-regulatory cell subset has been described which is able to suppress antigen-specific immune responses in vitro and in vivo. See,.e.g., U.S. Ser. No. 07/846,208, filed Mar. 4, 1992; U.S. Ser. No. 08/643,810, filed May 6, 1996; and Groux, et al. (1997) *Nature* 389:737–742; each of which is incorporated herein by reference. These T cells appeared to arise after antigenic stimulation with antigen presenting cells, in the presence of exogenously added IL-10. These cells had regulatory capacity in that they inhibited the development of inflammatory bowel disease as well as T cell proliferation in vitro.

The cells are useful in that they exhibit a bystander effect, e.g., suppressing immune responses in other cells exposed to the same antigen. Thus, administration of regulatory T cells can suppress the induction of a response upon stimulation or exposure of antigen to these other cells. This property is important in the context of, e.g., suppression of response to transplantation antigens. If regulatory T cells specific for the donor antigens are available and administered to a recipient, the tissue rejection response may be suppressed. Conversely, in a bone marrow transplant, the graft immune response to host antigens may be suppressed.

Since the early methods were described, similar culture conditions have not given rise to homogeneous IL-10-producing cells. The cultures are always contaminated with IL-4-producing Th2 cells, possibly as a result of the poor growth capacity of the regulatory T cells. Type 1 T-regulatory (Tr1) cells are defined, in part, by their unique cytokine profile: they produce high levels of IL-10, significant levels of TGF-β, IL-5, and IFN-γ, but no significant amounts of IL-4 or IL-2.

Many different ways were tested for isolating such homogeneous populations of CD4+ T cells, producing essentially only IL-10 and very low amounts of other tested cytokines. Immunosuppressive drugs were evaluated for their capacity to support production of such cells. To this end it was shown that culturing antigen specific CD4+ T cells with antigen and antigen presenting cells (APC) with a combination of the immunosuppressive agents Vitamin D3 (VitD3) and Dexamethazone (Dex) gives rise to a homogeneous population of IL-10-producing cells, producing little to no IL-4, IL-5, or IFN-γ. Similarly, culturing antigen specific CD4+ T cells with antigen and T cell mitogens anti-CD3 and anti-CD28 (e.g., without APC) with a combination of VitD3 and Dex did likewise.

VitD3 on its own appears to drive the development of Th2 cells producing high levels of IL-4 and IL-5 and reduced IFN-γ. Dex alone partially inhibited both IL-4 and IL-5 and IFN-γ, and enhanced the production of IL-10. However, the cells proliferated only poorly and still produced some IL-4. The combination of both drugs led to an enhancement of IL-10 producing cells, even in the complete absence of IL-4. These resulting T cells are regulatory T cells, with properties which distinguish them from the Tr1 cells described above. In particular, these regulatory T cells do not produce IL-5 and are not IL-4 dependent.

However, the production of these IL-10 producing regulatory T cells and their proliferation is further enhanced by neutralization of IL-4, IFN-γ, and IL-12 in the same cultures with neutralizing mAbs to eliminate small numbers of Th1 or Th2 cells from developing. The process is independent of IL-4 and partially dependent on IL-10 (and in some cases TGF-β). This allows the isolation of large numbers of relatively homogeneous, antigen-specific, (predominantly only) IL-10 producing cells (since the treatment does not inhibit the proliferation of these cells).

This development of essentially IL-10 only producing cells using Vitamin D3 and Dexamethazone plus antigenic stimulation of CD4+ T cells has also been reproduced in human systems. In this case there is some dependency on IL-4, which is being further investigated.

Furthermore, these IL-10-producing T cells obtained in the mouse can inhibit the development of the autoimmune disease, experimental autoimmune encepahlomyelitis (EAE), a mouse model for multiple sclerosis (MS), provided that their specific antigen is coadministered to the brain. This demonstrates the immunoregulatory capacity of these T cells. As such, the cells exhibit properties to inhibit inflammatory pathologies in vivo, consistent with a label "regulatory T cells", which also applies to the Tr1 cells described above.

Glucocorticoids (GC), including Dexamethasone (Dex), are potent antiinflammatory and immunosuppressive agents that are widely used in the treatment of inflammatory disorders, such as autoimmune and allergic diseases (Wilckens and De Rijk (1997) *Immunol. Today* 18:418–424; Schleimer, et al. (eds.) (1997) *Inhaled Glucocorticoids in Asthma: Mechanisms & Clinical Actions, Marcel* Dekker, NY, NY. GC have been shown to have an inhibitory effect on both T cells and APC, at the level of proliferation as well as cytokine production, with down-regulation of IFN-γ, IL-4, and IL-5 under some conditions, but upregulation of IL-4 under other conditions. See Blofta, et al. (1997) *J. Immunol.* 158:5589–5595; Ramirez, et al. (1996) *J. Immunol.* 156: 2406–2412; and Daynes and Araneo (1989) *Eur. J. Immunol.* 19:2319–2325. This may result from indirect effects, e.g., GC down-regulate the production of IL-12 by APC and thus IFN-γ production by T cells (Blotta, et al. (1997) *J. Immunol.* 158:5589–5595; Vieira, et al. (1998) *J. Immunol.* 161: 5245–5251; and Visser, et al. (1998) *Blood* 91:4255–4264), and thus in some cases may indirectly upregulate the production of IL-4 (Blotta, et al. (1997) *J. Immunol.* 158: 5589–5595) and or IL-5 (Vieira, et al. (1998) *J. Immunol.* 161:5245–5251) and/or IL-10 (Vieira, et al. (1998) *J. Immunol.* 161:5245–5251; and Visser, et al. (1998) *Blood* 91:4255–4264) in cultures contain APC, antigen, and T cells. Recently, it has been shown that GC drive human CD8+ T cell differentiation towards a stable phenotype with high IL-10 and reduced IFN-γ, IL-4, IL-5 and IL-13 production. See Richards, et al. (2000) *Eur. J. Immunol.* 30:2344–2354.

GC bind the cytosolic GC receptor (GR), which then translocates to the nucleus and inhibits the transcriptional activation of target genes. See review of Karin, in Schleimer, et al. supra; and Karin (1998) *Cell* 93:487–490. GC mediate transcriptional repression through: 1) interfering with the function of transacting factors, such as AP-1 and NFκB (De Bosscher, et al. (1997) *Proc. Nat'l. Acad. Sci. USA* 94:13504–13509), via protein-protein interactions; and inhibition of NFAT binding to cytokine gene promoters (Chen, et al. (2000) *J. Immunol.* 164:825–832); 2) direct DNA binding to poorly conserved negative GC responsive elements (GRE); or 3) inducing the expression of inhibitory factors such as IkBa (reviewed in Karin in Schleimer, et al., supra. Furthermore, GR represses TGF-β transcriptional activation of the plasminogen activator PAI-1 gene in a ligand-dependent manner, by both Smad3 and Smad4 C-terminal activation domains. See Song, et al. (1999) *Proc. Nat'l Acad. Sci. USA* 96:11776–11781.

In the past few years it has become apparent that VitD3, in addition to its well known role in mineral and skeletal homeostasis, regulates the differentiation, growth and function of a broad range of cells, including cells of the immune system. See review by Lemire (1995) *J. Steroid Biochem. Mol. Biol.* 53:599–602; and Hewison, et al. (1992) *J. Endocrinol.* 132:173–175. The immunological effects of VitD3 were demonstrated as inhibition of autoimmune diseases including EAE. See Cantorna, et al. (1996) *Proc. Nat'l Acad. Sci. USA* 93:7861–7864; Mattner, et al. (2000) *Eur. J. Immunol.* 30:498–508; and review by Piemonti, et al. (2000) *J. Immunol.* 164:4443–4451. VitD3 has inhibitory effects on monocytes/macrophages/dendritic cells as well as on lymphocytes, and inhibits the production of a wide variety of cytokines including, e.g., IL-12, IL-1, IL-6, and TNF; as well as IL-2 and IFN-γ; and thus has been suggested to inhibit Th1 responses. See D'Amborsio, et al. (1998) *J. Clin. Invest.* 101:252–262; Piemonti, et al. (2000) *J. Immunol.* 164:4443–4451; and Lemire, et al. (1995) *J. Nutr.* 125: 1704S–1708S.

1,25(OH)-Dihydroxyvitamin D3 (VitD3) is a secosteroid receptor hormone that binds to a nuclear receptor named Vitamin D3 receptor (VDR). Once bound to the hormone ligand the receptor associates with specific recognition sequences called vitamin D responsive elements (VDRE) which are present in the promoter regions of target genes and are involved in regulating their transcription. Recent studies have shown that VitD3 represses IL-2 gene transcription by VDR-dependent inhibition of NFATp/AP-1 complex formation. Alroy, et al. (1995) *Mol. Cell Biol.* 15:5789–5799. In addition, it has also been reported that VitD3 mediates downregulation of NF-kB activation by decreasing NF-kB p50 and c-Rel expression in T cells. Yu, et al. (1995) *Proc.*

*Nat'l Acad. Sci. USA* 92:10990–10994. The inhibition of transcription activation of the IL-12 p35 and p40 genes by VitD3 may be, in part, by downregulation of NF-kB activation and binding to the p40-kB sequence. D'Ambrosio, et al. (1998) *J. Clin. Invest.* 101:252–262. In addition, SMAD3, one of the SMAD proteins downstream in the TGF-β signaling pathway, which was inhibited by GC, acts as a coactivator specific for ligand-induced transactivation of VDR. Yanagisawa, et al. (1999) *Science* 283:1317–1321.

The practical application of these immunoregulatory T cells includes their use in vivo to inhibit immune pathologies. See, e.g., U.S. Ser. No. 60/225,502, which is incorporated herein by reference. The antigen specific bystander effect is important in the capacity to prevent response in other T cells upon stimulation with that same antigen or with a different antigen presented at exactly the same time. Thus, the development of regulatory T cells to an identified antigen can be transferred to a host by administering these regulatory T cells together with their specific antigen. One example using the same antigen is in tissue transplantation or in the inhibition of graft-versus-host-disease (gvhd) during bone marrow transplantation. In this context, researchers recently initiated clinical trials in Italy for the inhibition of alloantigen response. At present the trials involve adoptive immunotherapy using T lymphocytes tolerized in vitro with interleukin-10 in patients with T-cell depleted allogeneic stem cells from non compatible (haploidentical) related donors. This strategy is based, in part, on the earlier findings of Groux, et al. describing the production of anergic and T regulatory CD4+ populations in the presence of IL-10.

The present invention provides means for adoptive immunotherapy using T cells which have been rendered suppressive in vitro by culture in VitD3 and Dex. The advantages of the present method include: that it gives rise to a homogeneous population of IL-10-producing cells, producing little to no IL-4, IL-2, IL-5, or IFN-γ, with regulatory capacity in vivo; and these cells can proliferate and thus can be generated in bulk, in a timely fashion. If a donor is identified, the regulatory T cells may be prepared and administered to the immune system which will respond to non-self antigens.

In the case of immunopathologies where the antigen is unknown, e.g., inflammatory bowel disease (IBD), rheumatoid arthritis (RA), multiple sclerosis (MS), and diabetes, these regulatory T cells can still be used provided that the specific antigen for the regulatory cells is simultaneously delivered with the cells while pathology producing T cells are also activated in vivo. For example, CNS antigens implicated in multiple sclerosis include MBP and MOG, although T cells recognizing other CNS antigens may be pathogenic. In principle, MBP and MOG specific T cells can be expanded from PBL of MS patients in the presence of VitD3/Dex, thereby generating T regulatory cells after stimulation. These regulatory T cells can then be infused back into the patient together with the soluble antigen, preferably simultaneously. A similar strategy can be used for other inflammatory or autoimmune pathologies.

The qualitative characteristics of many immune responses are regulated by T-cell subsets through their production of distinctive cytokines. Two well-characterized T-cell subsets are the Th1 cells that, via production of IFN-γ, promote cell-mediated responses against bacteria, and Th2 cells that, by producing IL-4, IL-5, and IL-13, promote antibody production, and the anti-parasite allergic mast cell and eosinophil responses. Abbas, et al. (1996) *Nature* 383: 787–793. Both of those T helper subsets originate from a naive T-cell precursor, whose differentiation is influenced by both the manner and the environment in which it is initially stimulated. Variables known to influence the development of T-cell subsets include the affinity of the TCR for antigen (Constant and Bottomly (1997) *Ann. Rev. Immunol.* 15:297–322), the duration of the interaction between TCR and antigen (Iezzi, et al. (1999) *Eur. J. Immunol.* 29:4092–4101), and differential co-stimulation by APCs (McAdam, et al. (1998) *Immunol. Rev.* 165:231–247). However, the best defined differentiating factors are the cytokines present upon T cell activation. Thus, it is clear that the presence of IL-12 during priming favors the development of Th1 cells, whereas IL-4 favors the development of Th2 cells. O'Garra (1998) *Immunity* 8:275–283; Romagnani (1991) *Immunol. Today* 12:256–257; and Romagnani (1997) *Immunol. Today* 18:263–266.

Evidence has been provided for the existence of a CD4+ T cell subset, designated Tr1, which has a profile of cytokine production distinctive from classical Th1 or Th2 cells. Groux, et al. (1997) *Nature* 389:737–742. The present improvement to the production of IL-10 producing T regulatory cells using the VitD3/Dex method allows the isolation of a reproducibly homogeneous population of IL-10 producing cells that have a significant proliferative capacity.

In a murine model of inflammatory bowel disease (IBD) in SCID mice, co-transfer of Tr1 clones together with pathogenic CD4+CD45RB$^{hi}$ T cells prevented the induction of disease. Groux, et al. (1997) *Nature* 389:737–742. Prevention of IBD was only observed in mice that were administered the antigen recognized by Tr1 cells, demonstrating that Tr1 cells must be activated in vivo via the TCR to exert their regulatory effects. Similarly, T regulatory cells produced with the VitD3/Dex method can inhibit the inflammatory pathology EAE provided the specific antigen of the T regulatory cells is delivered virtually simultaneously.

Donor-derived T cells which were specific for host alloantigens which possessed a Tr1-profile of cytokine production have been isolated from tolerant SCID patients who had been reconstituted with HLA-mismatched. stem cells. Bacchetta, et al. (1994) *J. Exp. Med.* 179:493–502; Bacchetta, et al. (1993) *J. Clin. Invest.* 91:1067–1078; and Bacchetta, et al. (1990) *J. Immunol.* 144:902–908. Those data supported the hypothesis that Tr1 cells functioned as regulatory cells in vivo.

Other investigators had also reported the presence of (a) novel subset(s) of CD4+ T cells that secreted high levels of IL-10 and/or TGF-β, and that had regulatory activities similar to those described. Notably, in most cases, these regulatory cells appeared to arise following repeated antigen stimulation either in vitro or in vivo. Buer, et al. (1998) *J. Exp. Med.* 187:177–183 reported that IL-10-producing T cells were generated in vivo following repeated antigen stimulation, and that although these T cells were unable to proliferate in vitro, they could nevertheless produce high levels of IL-10 and regulate immune responses to influenza hemagglutinin. Similarly, repetitive in vitro stimulation with antigen-loaded APC (Chakraborty, et al. (1999) *J. Immunol.* 162:5576–5583) or in vivo stimulation with superantigen (Miller, et al. (1999) *J. Exp. Med.* 190:53–64; and Sundstedt, et al. (1997) *J. Immunol.* 158:180–186), lead to the emergence of CD4+ T cells that suppressed naive T-cell responses via an IL-10-dependent mechanism. A number of investigators had also documented the presence of antigen-specific regulatory CD4+ T cells that, via a TGF-β-dependent mechanism, could prevent T cell-mediated diseases. Chen, et al. (1994) *Science* 265:1237–1240; Powrie, et al. (1996) *J. Exp. Med.* 183:2669–2674; Han, et al. (1996) *J. Autoimmun.* 9:331–339; Bridoux, et al. (1997) *J. Exp. Med.* 185:1769–1775; and Khoo, et al. (1997) *J. Immunol.* 158:

3626–3634. Thus, there is now a large body of evidence that supports the notion that clonal suppression mediated by regulatory cells which produce suppressive cytokines can be an important mechanism of peripheral tolerance. This is in addition to the well recognized mechanisms of clonal deletion and clonal anergy. The regulatory T cells provided herein will share most of the regulatory characteristics of the Tr1 cells.

Culture conditions were developed to induce the differentiation of polarized populations of CD4+ T cells that produced IL-10 and displayed immunoregulatory properties.

II. Regulatory T Cell Differentiation

The derivation in IL-10, or in IL-10 plus TGF-$\beta$, or IL-10 plus IFN-$\alpha$, of T regulatory cells (see U.S. Ser. No. 07/846,208, filed Mar. 4, 1992; U.S. Ser. No. 08/643,810, filed May 6, 1996; and Groux, et al. (1997) Nature 389:737–742) producing IL-10, and inhibiting immunopathology, appears not to yield a homogeneous population of cells, and the cells proliferate poorly. The reason may be because this is not the complete molecular mechanism for the differentiation of such regulatory T cells. To improve this method, herein is described the use of immunosuppressive drugs for the development of homogeneous populations of T regulatory cells producing only IL-10. The regulatory T cells can arise from naive CD4+ T cells, e.g., from mouse spleen or human cord blood and peripheral blood.

Culture of antigen specific naive splenic CD4+ T cells from DO11.10 mice which are transgenic for a TCR specific for the antigen $OVA_{323-339}$, with antigen and APC in a combination of the immunosuppressive agents Vitamin D3 and Dexamethazone gives rise to a homogeneous population of IL-10-producing cells, producing little to no IL-4, IL-5, or IFN-$\gamma$. In addition naive splenic CD4+ T cells stimulated with the mitogens anti-CD3 and anti-CD28 in the presence of Vitamin D3 and Dexamethasone also gave rise to such IL-10 producing cells. VitD3 on its own appears to drive the development of Th2 cells producing high levels of IL-4 and IL-5 and reduced IFN-$\gamma$. Dex alone inhibited both IL-4 and IL-5 and IFN-$\gamma$, although not completely, and enhanced production of IL-10. The combination of both drugs led to an enhancement of IL-10 producing cells, even in the complete absence of IL-4. This is further enhanced by neutralization of IL-4, IFN-$\gamma$, and IL-12 in the same cultures with neutralizing mAbs to eliminate small numbers of Th1 or Th2 cells from developing. This also led to highly increased numbers of T cells producing IL-10. The process of development of IL-10 producing cells is independent of IL-4 and partially dependent on IL-10 (and in some cases TGF-$\beta$). This allows the isolation of large numbers of relatively homogeneous, antigen-specific, IL-10 only producing cells, in large numbers (since the treatment does not inhibit the proliferation of these cells). Two rounds of stimulation are much preferred. IL-2 is present in the culture after the first 3 days of activation. VitD3 is used at $4\times10$-8 M (preferably in the range $4\times10$-9 M to $4\times10$-7 M) while DEX is used at 10-8M (preferably in the range of 10-9 M to 10-7 M).

Stimulation of naive T cells (CD4+CD62L+) using Antigen Presenting Cells (APC) in the presence of VIT D3 and DEX gives rise to: about 60% IL-10 positive cells (producing at least 500 ng of IL-10 per 106 cells); about 10% IL-10 and IL-4 double positive cell (producing about 50 ng of IL-4 per 106 cells); less than about 1% IL-5 positive cells (producing less than about 30 pg of IL-5 per 106 cells); and less than about 5% IFN-$\gamma$ positive cells (producing less than about 40 ng of IFN-$\gamma$ per 106 cells). The cytokine profiles produced by the cells after restimulation are evaluated after 6 h by FACS analysis, while the quantities are accumulated by the respective cell population in 1 ml for 48 h.

Alternatively, stimulation of naive T cells using Antigen Presenting Cells (APC) in the presence of VitD3 and Dex+anti-IL-4+anti-IL-12+anti-IFN-$\gamma$ gives rise to a population of cells: about 25–35% IL-10 positive cells (producing at least about 100 ng of IL-10 per 106 cells); less than about 1% IL-4 positive cells (producing about 30–1000 pg of IL-4 per 106 cells); less than about 1% IL-5 positive cells (producing less than about 30 pg of IL-5 per 106 cells); less than about 1% IFN-$\gamma$ positive cells (producing less than about 30 pg of IFN-$\gamma$ per 106 cells); and less than about 5% IL-2 positive cells (producing about 30–350 pg IL-2 per 106 cells).

If the stimulation of naive T cells is performed in the presence of anti-CD3+anti-CD28 with VitD3 and Dex, the resulting population of cells is: about 70–75% IL-10 positive cells; less than about 2% IL-4 positive cells; and less than about 2% IL-5 positive cells; less than about 1% IFN-$\gamma$ positive cells; and less than about 2% IL-2 positive cells. Corresponding quantities of cytokines should be detected according to the cell types described immediately above.

Stimulation of naive T cells using anti-CD3+anti-CD28 in the presence of VitD3 and Dex+anti-IL-4+anti-IL-12+anti-IFN-$\gamma$ gives rise to a population of: about 60% IL-10 positive cells; less than about 1% IL-4 positive cells; less than about 1% IL-5 positive cells; less than about 1% IFN-$\gamma$ positive cells; and about 10% IL-2 and IL-10 double positive cells.

This data on the development of IL-10 only producing cells using Vitamin D3 and Dexamethazone plus antigenic stimulation of CD4+ T cells has also been reproduced in human systems. In this case there is some dependency on IL-4. Stimulation of purified human naive T cells from cord-blood (CD4+CD45RA+) using L cells (expressing CD32, CD86) as APC plus anti-CD3 in the presence of VitD3 and Dex gives rise after one week of stimulation to a majority of IL-10 producing T cells: VitD3 is used at $2\times10$-8 M($2\times10$-9 M to $2\times10$-7 M) while Dex is used at 10-7 M (10-8 M to 10-6 M). In addition, stimulation of purified naive T cells enriched from human peripheral blood (CD4+CD45RA+) using anti-CD3/+/− anti-CD28, in the presence of VitD3 and Dex gives rise after one week of stimulation to a majority of IL-10 producing T cells.

Furthermore, the IL-10-producing T cells obtained in the mouse can inhibit the development of the autoimmune disease, experimental autoimmune encepahlomyelitis (EAE) provided that their specific antigen is coadministered to the brain, demonstrating the immunoregulatory capacity of these T cells. The mechanisms of their action is being investigated. Cells driven as described above have been shown to protect mice against EAE (a mouse model of Multiple Sclerosis) in a bystander way provided their specific antigen is injected simultaneously. However, the effect may not require a bystander mechanism.

III. Uses

The present invention also provides efficient methods for preparing and using antigen-specific regulatory T cells. See, e.g., Paul (ed. 1997) *Fundamental Immunology* Raven Press. The regulatory effect seems to be maintained for a period of time, e.g., for at least about 14 days, 18 days, 21 days, 24 days, etc. The lack of responsiveness may remain for weeks, months, and preferably years.

This antigen-specific regulation results in a form of tolerance in the pathogenic T cells by active suppression via regulatory T cell factors. Such regulatory T cells can be produced by presenting naive T cells and antigen presenting cells (APC) with a combination of IL-10 with antigen. Contacting with Vitamin D3 and Dexamethasone provides greater purity. Many fewer cells are generated which produce IL-4, IL-5, IFN-γ, or IL-2. The contacting typically is repeated at least once, and preferably twice or more. Each contacting is generally performed for about a week each, as the cells seem to lose viability if subjected to continuous stimulation. Additionally, particular growth factors might become depleted in the cultures.

Alternatively, the naive cells may be contacted with a different antigen stimulating signal, e.g., with a combination of anti-CD3 and anti-CD28. The Vitamin D3 and Dexamethasone are added, again for the appropriate amount of time, preferably at least two rounds for a week each. The resulting regulatory T cells make up about 70–75% IL-10 producing cells.

Yields are dramatically improved by inclusion of one or more of anti-IL-4, anti-IL-12, and anti-IFN-γ. The components are presented to the immune system, or cells thereof, for adequate periods of time, often completely coextensive, though the period may not necessarily require both components for the entire duration. This period will typically be at least about 5 days, more typically at least about 7 days, preferably at least about 9–11 days, and more preferably at least about 13–15 days or more. The dosing of the VitD3, Dex, and or antigen stimulating signal may depend on various factors, including, e.g., the antigen, the duration of the periods, what combinations of signals and factors are present, whether the VitD3/Dex is presented before antigen, etc. Preferably, the components are presented together for at least about 7 days. Blocking of IFN-γ and/or IL-4 signals with antagonists, e.g., anti-IFN-γ or anti-IL-4 antibodies, greatly improves the purity.

IL-10 has been described before. See, e.g., deVries and de Waal Malefyt (eds. 1995) *Interleukin*-10 Landes, Austin, Tex. Other means to effect higher IL-10 levels have been described, and include stimulation of endogenous IL-10, including, e.g., LPS, TNF-α, IL-12, BCG1 (Bacillus Calmett Guerin), *Corynebacterium parvus*, poly I-C (alloadjuvant for activating monocytes and macrophages), etc. However, these stimuli do not lead to a homogeneous population of cells producing essentially IL-10 only. Using VitD3/Dex, such cells can be achieved, and the absence of production of other cytokines both reflects a homogeneity of cells in the resulting population, and prevents the differentiation of cells to other T helper subsets.

Various types of antigens exist for which antigen-specific regulatory cells may be important. Both alloantigens and self antigens are presented in the context of MHC. See, e.g., Paul (ed.) *Fundamental Immunology*. Other antigens for which T cell regulation may be important include soluble antigens, e.g., soluble proteins or fragments of insoluble complexes, particulate antigens, e.g., bacteria or parasites, and allergens. Various forms of antigen will be presented with VitD3/Dex to induce antigen-specific suppression. The described method yields homogeneity, probably because there is blocking of Th1 specific cytokines (e.g., with anti-IFN-γ and anti-IL-12) and Th2 specific cytokines (e.g., with anti-IL-4). The T regulatory cells derived in VitD3/Dex, as described, exhibit the production of IL-10, but essentially no IL-2, IFN-γ, IL-4, or IL-5, and they can block inflammatory pathology in vitro, e.g., in an EAE model.

The response to subsequent anti-CD3 with anti-CD28 antibody general stimulation, e.g., through the T cell receptor/CD3 complex, can be quantitated by analyzing cytokine production. Cytokines may be measured according to biological activity. Preferably, a quantitation of accumulated protein may be determined by various immuno-, activity, or other assays. Alternatively, mRNA production may be measured to establish levels of stimulation of transcription.

Typically, cytokines are measured after accumulation of secreted protein over set periods of time upon subsequent, e.g., secondary or subsequent, stimulation using anti-CD3 (e.g., from about 2–25 μg/ml, preferably about 10) with anti-CD28 (e.g., from about 1–10 μg/ml, preferably about 5) antibody or cognate antigen. Thus, the time for accumulation is preferably at least about 24 h in a volume of about 1 ml, but may be longer. Flow cytometric analysis of intracellular cytokine production using labeled anti-cytokine antibodies after Brefeldin A treatment may also be applied.

The measurement of cytokine production is after restimulation of T regulatory cells with the specific antigen, although more usually after generic stimulation with anti-CD3 (in vitro at about 10 μg/ml or more), which apparently activates through the T cell receptor. This stimulation results in a distinguishable cytokine production profile. Among the notable differences in cytokine production after restimulation are undetectable IL-4, IL-5, IL-2, and IFN-γ, and high IL-10 production.

The duration of VitD3/Dex with antigen can affect the extent of reversibility. Treatments over about 14 days with antigen and APC leads to substantial irreversibility.

IL-10 inhibited, in a dose-dependent fashion, the antigen-induced Th1 proliferative responses and cytokine production in the presence of APC (macrophages and dendritic cells). See Moore, et al. (1993) *Ann. Rev. Immunol.* 11:165–190. The suppressive effect was optimal when IL-10 was added at the beginning of the cultures suggesting that it acts on the early stages of T cell activation. Such responses were enhanced in the presence of anti-IL-10 mAb, indicating that endogenously produced IL-10 suppresses proliferation and IFN-γ production by Th1 when stimulated with antigen and APC. Inhibitory effects of IL-10 have also been observed irrespective of when irradiated human allogeneic peripheral blood mononuclear cells (PBMC), purified monocytes, or B cells were used as stimulator cells. The production of IL-2, IFN-γ, IL-6, GM-CSF, and TNF-α in primary MLR was diminished by IL-10 and enhanced in the presence of anti-IL-10 mAb. The strongest effects were observed on the production of IFN-γ.

Mouse and human IL-10 inhibit the synthesis of IFN-γ and granulocyte-macrophage colony stimulating factor (GM-CSF) induced in human Th1 cells and PBMC by PHA, anti-CD3 mAb, and IL-2 (Bacchetta, et al. (1989) *J. Immunol.* 144:902; and Bevan (1984) *Immunol Today* 5:128) in the presence of APC. See Moore, et al. (1993) *Ann. Rev. Immunol.* 11:165–190. This inhibition occurs at the transcriptional levels (Altmann, et al. (1989) *Nature* 338:512; Bacchetta, et al., supra). Murine IL-10 (m-IL-10) has pleiotropic activities on different cell types, including growth promoting effects on thymocytes (Chen, et al. (1991) *J. Immunol.* 147:528), cytotoxic T cells (De Koster, et al. (1989) *J. Exp. Med.* 169:1191), and mast cells (de Waal Malefyt, et al. (1991) *J. Exp. Med.* 174:1209). m-IL-10 induces class II MHC antigen expression on B cells and sustains the viability of these cells (de Waal Malefyt, et al. (1991) *J. Exp. Med.* 174:915). Furthermore, IL-10 inhibits cytokine production by macrophages (Bejarano, et al. (1985) *Int. J. Cancer* 35:327; Fiorentino, et al. (1989) *J. Exp. Med.* 170:2081). h- and m-IL-10 have extensive homology to BCRF-1, an open reading frame of the Epstein Barr virus (EBV) genome (Azuma, et al. (1992) *J. Exp. Med.* 175:353;

Bacchetta, et al. (1989) *J. Immunol.* 144:902). The protein product of BCRF-1, designated viral IL-10 (v-IL-10), shares most properties with h-and m-IL-10 including CSIF activity on human and mouse T cells (Bacchetta, et al., supra; Bevan, M. J., supra).

h-IL-10 and v-IL-10 inhibit antigen specific proliferative responses by reducing the antigen presenting capacity of human monocytes via downregulation of class II MHC molecules (Figdor, et al. (1984) *J. Immunol. Methods* 68:68). Moreover, IL-10 inhibits cytokine synthesis by LPS or IFN-γ activated monocytes, including CM-CSF, G-CSF, and the proinflammatory cytokines IL-1α, IL-1β, IL-6, IL-8, and TNF-α (Bejarano, et al. (1985) *Int. J. Cancer* 35:327; Fiorentino, et al, supra.). Interestingly, LPS activated monocytes produce high levels of IL-10, and enhanced production of cytokines was observed in the presence of anti-IL-10 mAb indicating an autoregulatory effect of IL-10 on monokine production (Bejarano, et al., supra).

Alloreactivity reflects, at least in part, recognition of foreign MHC molecules plus antigenic peptides of various origin (Fiorentino, et al. (1991) *J. Immunol.* 146:3444; Fiorentino, et al. (1991) *J. Immunol.* 147:3815; Freedman, et al. (1987) *J. Immunol.* 139:3260; Go, et al. (1990) *J. Exp. Med.* 172:1625). Moreover, alloreactive T cells may recognize conformational differences between MHC molecules largely independent of the peptides bound, or even on empty MHC molecules (Harding, et al. (1990) *Proc. Natl. Acad. Sci. USA* 87:5553; Hsu, et al. (1990) *Science* 250:830; Julius, et al. (1973) *Eur. J. Immunol.* 3:645). IL-10 inhibits allospecific proliferative responses, and cytokine production. In addition, the reduced proliferative responses could not be restored by exogenous IL-2.

Thus, the present invention provides means to generate large quantities of alloantigen specific T regulatory cells by stimulating host derived CD4+ T cells with donor derived irradiated PBMC in the presence of VitD3/Dex, e.g., for minimally at least about 3 days, preferably at least about 5 days, more preferably at least about 7 days, and in certain embodiments 9, 11, 13, 15, or more days. Methods are provided to increase yields of T regulatory cells, allowing for more effective therapeutic application. The cells can be administered prior or simultaneously with the transplant (organ or bone marrow). The transplant event and/or therapy may be with or without administration of VitD3/Dex.

The above cell therapy can be extended to treat other chronic diseases caused by antigens, such as gliadin (e.g., gluten) for the treatment of coeliac disease, allergens for the treatment of chronic allergic diseases (asthma, atopic dermatitis, rhinitis), or GAD (glutamic acid decarboxylase) or insulin for the treatment of diabetes.

In addition, this may provide treatment for inappropriate sensitivity to many other potential autoantigens. The cells or treatment may provide means for induction of long term tolerance and T regulatory cell development in vivo. Long term, e.g., 5–15 day treatment with VitD3/Dex may enhance in vivo production of suppressive cells, with copresentation of appropriate MHC antigens, e.g., with class I or class II, or other soluble antigens.

The invention also provides means for administration of VitD3/Dex in order to induce antigen specific regulatory T cells and long term antigen specific tolerance in vivo for the treatment of diseases with undesired T-cell activation, e.g., in transplant rejection, graft versus host disease, parasitic diseases, chronic inflammatory diseases such as Crohn's disease, colitis, chronic inflammatory eye diseases, chronic inflammatory lung diseases, and chronic inflammatory liver diseases. See, e.g., Frank, et al. (eds.) *Samter's Immunologic Diseases* Little, Brown, Boston, Mass.

If non-toxic derivatives of VitD3 are available, these may be delivered with appropriate corticosteroids with antigen in order to induce autoantigen specific regulatory T cells and autoantigen specific tolerance in vivo. This may be used for the treatment of autoimmune diseases such as rheumatoid arthritis, diabetes, and multiple sclerosis.

In many embodiments, the VitD3/Dex should be typically administered for a minimum of 5–15 days, preferably at least about 7 days.

When administered parenterally the regulatory T cells with antigen or the drugs VitD3/Dex with antigen will be formulated in a unit dosage injectable form (solution, suspension, emulsion) in association with a pharmaceutically acceptable parenteral vehicle. Such vehicles are inherently nontoxic and nontherapeutic. The regulatory T cells or drugs with antigen may be administered in aqueous vehicles, such as saline, or buffered vehicles with or without various additives and/or diluting agents. They will normally be administered intravenously, though it may be possible to administer as a subcutaneous (SQ), intradermal (ID), or intramuscular (IM) injection. The proportion of therapeutic entity and additive can be varied over a broad range so long as all are present in effective amounts. The therapeutic is preferably formulated in purified form substantially free of aggregates, other proteins, endotoxins, and the like, at concentrations of about 5 to 30 mg/ml, preferably 10 to 20 mg/ml. Preferably, the endotoxin levels are less than 2.5 EU/ml. See, e.g., Avis, et al. (eds. 1993) *Pharmaceutical Dosage Forms: Parenteral Medications* 2d ed., Dekker, N.Y.; Lieberman, et al. (eds. 1990) *Pharmaceutical Dosage Forms: Tablets* 2d ed., Dekker, N.Y.; Lieberman, et al. (eds. 1990) *Pharmaceutical Dosage Forms: Disperse Systems* Dekker, N.Y.; Fodor, et al. (1991) *Science* 251:767–773; Coligan (ed.) *Current Protocols in Immunology* Hood, et al. *Immunology* Benjamin/Cummings; Paul (ed. 1997) *Fundamental Immunology* 4th ed., Academic Press; Parce, et al. (1989) *Science* 246:243–247; Owicki, et al. (1990) *Proc. Nat'l Acad. Sci. USA* 87:4007–4011; and Blundell and Johnson (1976) *Protein Crystallography,* Academic Press, New York.

Preferably, an administration regimen maximizes the amount of therapeutic delivered to the patient consistent with an acceptable level of side effects. Accordingly, the amount of therapeutic delivered depends in part on the particular circumstances and the severity of the condition being treated.

Determination of the appropriate dose, e.g., of regulatory T cells and soluble antigen (e.g., bystander or specific for pathogenic T cells), is made by the clinician, e.g., using parameters or factors known in the art to affect treatment or predicted to affect treatment. Generally, the dose begins with an amount somewhat less than the optimum dose and it is increased by small increments thereafter until the desired or optimum effect is achieved relative to any negative side effects. Preferably, a therapeutic that will be used is derived from the same species as the animal targeted for treatment, thereby minimizing a humoral response to the reagent.

In particular contexts, e.g., transplant, may involve the administration of the therapeutics in different forms. For example, in an organ transplant or skin graft, the tissue may be immersed in a sterile medium containing the therapeutic resulting in a prophylactic effect on cell migration soon after the transplant is applied.

The phrase "effective amount" means an amount sufficient to effect a desired response, or to ameliorate a symptom or sign of the medical condition. Typical mammalian hosts will include mice, rats, cats, dogs, and primates, including humans. An effective amount for a particular patient may vary depending on factors such as the condition being treated, the overall health of the patient, the method, route, and dose of administration and the severity of side affects. Preferably, the effect will result in a change in quantitation of at least about 10%, preferably at least about 20%, 30%, 50%, 70%, or even 90% or more. When in combination, an effective amount is in ratio to a combination of components and the effect is not limited to individual components alone.

An effective amount of therapeutic will modulate the symptoms typically by at least about 10%; usually by at least about 20%; preferably at least about 30%; or more preferably at least about 50%. Such will result in, e.g., statistically significant and quantifiable changes. This may be an increase or decrease in the numbers of target cells being attracted within a time period or target area.

The present invention provides reagents and methods which will find use in therapeutic applications as described. See, e.g., Berkow (ed.) *The Merck Manual of Diagnosis and Therapy.* Merck & Co., Rahway, N.J.; Thorn, et al. *Harrison's Principles of Internal Medicine.* McGraw-Hill, NY; Gilman, et al. (eds. 1990) *Goodman and Gilman's: The Pharmacological Bases of Therapeutics.* 8th Ed., Pergamon Press; *Remington's Pharmaceutical Sciences.* 17th ed. (1990), Mack Publishing Co., Easton, Pa.; Langer (1990) *Science* 249:1527–1533; and *Merck Index,* Merck & Co., Rahway, N.J.

Antibodies to cytokines, e.g., IL-10, may be used for the identification or sorting of regulatory T cell populations. See Scheffold, et al. (2000) *Nature Med.* 6:107–110. Methods to sort such populations are well known in the art, see, e.g., Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y. Populations of cells can also be purified, e.g., using magnetic beads as described, e.g., in Bieva, et al. (1989) *Exp. Hematol.* 17:914–920; Hernebtub, et al. (1990) *Bioconj. Chem.* 1:411–418; Vaccaro (1990) *Am. Biotechnol. Lab.* 3:30.

The broad scope of this invention is best understood with reference to the following examples, which are not intended to limit the inventions to the specific embodiments.

EXAMPLES

I. General Methods

Some of the standard methods are described or referenced, e.g., in Maniatis, et al. (1982) *Molecular Cloning. A Laboratory Manual,* Cold Spring Harbor Laboratory, Cold Spring Harbor Press; Sambrook, et al. (1989) *Cloning: A Laboratory Manual,* (2d ed.), vols. 1–3, CSH Press, NY; Ausubel, et al., *Biology,* Greene Publishing Associates, Brooklyn, N.Y.; or Ausubel, et al. (1987 and Supplements) *Current Protocols in Molecular Biology,* Greene/Viley, New York; Innis, et al. (eds.)(1990) *PCR Protocols: A Guide to Methods and Applications* Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology,* vol. 182, and other volumes in this series; manufacturer's literature on use of protein purification products, e.g., Pharmacia, Piscataway, N.J., or Bio-Rad, Richmond, Calif.; and Coligan, et al. (eds.) (1995 and periodic supplements) *Current Protocols in Protein Science,* John Wiley & Sons, New York, N.Y. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *QIAexpress: The High Level Expression & Protein Purification System* QIAGEN, Inc., Chatsworth, Calif.

Standard immunological techniques are described, e.g., in Hertzenberg, et al. (eds. 1996) *Weir's Handbook of Experimental Immunology* vols. 1–4, Blackwell Science; Coligan (1991) *Current Protocols in Immunology* Wiley/Greene, NY; and *Methods in Enzymology* volumes. 70, 73, 74, 84, 92, 93, 108, 116, 121, 132,150, 162, and 163.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Mouse Cell Methodology

DO.11.10 mice transgenic for an ovalbumin$_{323-339}$ specific $\alpha\beta$TCR were used as a source of antigen specific T cells. See Murphy, et al. (1990) *Science* 250:1720–1727. They were backcrossed on to a BALB/C background and (DO11.10×BALB/C)F$_1$ mice were used as the source of T cells in all experiments. BALB/C (Taconics, Germantown, N.Y.) mice were used to provide splenic antigen presenting cells (APC).

Cytokines, Antibodies and Antigen

Recombinant cytokines were used as follows: mouse IL-4 (DNAX, Palo Alto, Calif.), and mouse IL-12 (Pharmingen, San Diego, Calif.). Monoclonal anti-cytokine antibodies used in culture were anti-IL-4 (clone 11B11; see Ohara and Paul (1985) *Nature* 315:333–336), anti-IL-12 (clone C17.8.20, a kind gift of G. Trinchieri, The Wistar Institute; Ozmen, et al. (1994) *J. Exp. Med.* 180:907–915), and anti-IFN-$\gamma$ (XMG 1.2, J. Abrams, DNAX). Anti-mouse CD3 and CD28 mAbs used for T cell stimulation were purchased from Pharmingen. MAbs used for T cell preparation were anti-B220, anti-CD8$\alpha$, anti-Mac-1, anti-CD4-FITC, and anti-L-selectin-PE (all mouse specific, Pharmingen). Tissue culture medium used was RPMI 1640 (JR Scientific Inc., Woodland, Calif.) supplemented with 10% fetal calf serum (heat inactivated for 1 h at 56° C., JR Scientific Inc.), 2-mercaptoethanol (0.05 mM, Sigma Chemical Co.), HEPES buffer (10 mM, Gibco BRL, Grand Island, N.Y.), penicillin (100 U/ml) and streptomycin (100 $\mu$g/ml, Gibco BRL), L-glutamine (2 mM, BioWhittaker, Walkersville, Md.), and sodium pyruvate (1 mM, BioWhittaker) (cRPMI).

Cell Culture

Naive CD4$^+$T cells were prepared according to Ferber, et al. (1999) *Clin. Immunol.* 91:134–144. Briefly, immunomagnetic depletion of CD8$\alpha^+$, B220$^+$, and Mac-1$^+$ splenocytes was performed using goat anti-rat Ig coated beads (Biomag, PerSeptive Biosystems, Framingham, Mass.). The depleted population was then stained with anti-CD4-FITC and anti-L-selectin-PE and CD4$^+$ L-selectin$^{high}$ cells were sorted using a FACStar$^{Plus}$ cell sorter (Becton-Dickinson, Mountain View, Calif.). The purities achieved were >98%, and staining these cells did not alter their function. Cultures were established with either antigen and antigen presenting cells, or anti-CD3 and anti-CD28. In the former case, cultures were set up in 2 ml in 24 well plates with $2.5 \times 10^5$ sorted naive T cells, $5 \times 10^6$ splenic APC (red blood cell lysed and γ-irradiated to 3000 rad) and 0.6 μM $OVA_{323-339}$ peptide. In the latter case, 24 well plates were coated with anti-CD3 in PBS (10 μg/ml, 0.5 ml per well) for at least 2 h at 37° C. in a humidified incubator pulsed with $CO_2$, wells were washed twice with cRPMI before use; soluble anti-CD28 was added to the cultures at 1 μg/ml and cultures were at $10^6$ cells per well. Vitamin D3 (BIOMOL Research Labs, Plymouth Meeting, Pa.) was used at $4 \times 10^{-8}$ M, Dexamethasone (SIGMA) was used at $10^{-8}$ M. Both were present during the entire time of the stimulation process. After 3 days, cultures were split 1:3 with addition of IL-2, and in the case of cultures stimulated with anti-CD3 and anti-CD28, cells were placed in fresh wells. After 6 days, T cells were harvested, counted, and restimulated at $2.5 \times 10^4$ per well in 200 μl in 96 well plates for phenotype analysis by cytokine secretion. Wells were then again coated with anti-CD3 at 10 μg/ml and anti-CD28 was used at 1 μg/ml in solution. Alternatively, $5 \times 10^5$ irradiated APC were used per well with OVA peptide at 0.6 μM, or PMA/Ionomycin stimulations were used. Supernatants were harvested at 48 h for assessment of cytokines. T cells were also characterized by immunofluorescence staining and flow cytometric analysis. Cells were stimulated with PMA (50 ng/ml) and ionomycin (500 ng/ml) at $1 \times 10^6$ cells/ml in 24 well plates; after 2 h Brefeldin A (10 ng/ml) was added and 2 h later the cells were harvested and fixed with 2% paraformaldehyde (SIGMA). Cells were permeabilized with 0.5% saponin and stained with the cytokines antibodies. The cells were analyzed using a FACScan flow cytometer (Becton-Dickinson).

III. Human Cell Purification

Peripheral blood mononuclear cells (PBMC) were isolated from peripheral blood, freshly collected into sodium citrate, by centrifugation on a Lymphoprep (Nycomed, Birmingham, UK) density gradient. Donors were healthy at the time of the study. PBMC were positively selected for CD8+ or CD4+ T cells using antibody-coated magnetic beads and Detach-a-beads (Dynal (UK), Wirral, GB) according to the manufacturer's guidelines. Alternatively, PBMC were depleted of CD4+ or CD8+ T cells by negative selection using antibody-conjugated magnetic beads to give CD8+ APC or CD4+ APC populations, respectively. CD4+ T cells were further subdivided into naive CD45RA+ and antigen-experienced CD45RO+ populations using specific antibodies (PharMingen) and negative selection with magnetic beads. APC consisted predominantly of CD4low, CD14+ monocytes (13–28%), although a minor population (1.3–5%) of CD4low, CD14– cells is likely to contain DC. Isolated populations were washed and resuspended at $1 \times 10^6$/ml in RPMI 1640 (Life Sciences, Abingdon, GB) containing 10% heatin-activated FCS (PAA Laboratories, Oxford, GB), 2 mM L-glutamine, and 50 μg/ml gentamycin (both from Life Sciences). Cell purity was assessed by flow cytometry using a FACScan (Becton Dickinson, Abingdon, GB) and Lysis 2 software. Anti-CD4 (Leu-3a) and CD14 (Leu-M3) antibodies were purchased from Becton Dickinson; CD3 (UCHT1), CD8 (UCHT4), isotype-matched control IgG1 (MOPC21), and IgG2b (MOPC141) antibodies were from Sigma (Poole, GB).

Human neonatal leukocytes were isolated from freshly collected neonatal blood by density gradient centrifugation using Histopaque 1077 (Sigma). Adherents cells were removed by incubation of the cells on a plastic petri dish (Falcon; Becton-Dickinson) for 1 h at 37° C. in the presence of 6 μg of DNase (Sigma). Neonatal CD4+ T cells were then isolated from nonadherent lymphocytes using magnetic microspheres. Nonadherent cells were incubated with anti-CD4 mAb-coated Dynabeads and CD4+ T cells were isolated by exposure to a magnetic field (Dynal) according to manufacturer's instructions. Cells were washed five times with PBS containing 2% FCS and the beads-cells complexes were incubated with Dynal Detach-a-beads reagents for 1 h with vigorous shaking. The purity of the positively selected neonatal CD4+ T cells using this procedure was typically >97% as determined by flow cytometry.

Human Cell Culture and Stimulation

Purified T cells from PBMC or T cells plus accessory cells (T+APC) at $1 \times 10^6$ in 1 ml were stimulated in 24-well tissue culture plates pre-coated with 1 μg/ml OKT-3 antibody (purified in-house) and previously determined optimal concentrations of human IL-2 (Eurocetus, Harefield, GB) with or without IL-4 (NBS, Hatfield, UK). Cells were incubated for up to 7 days at 37° C./5% $CO_2$ with a 50% change of media on day 3. On day 7 cells were washed and resuspended at $1 \times 10^6$/ml and cultured with anti-CD3 and IL-2 alone. Neonatal CD4+ T cells were stimulated using irradiated (7000 rad) L cells transfected with CD32, CD58, and CD80 in the presence of anti-CD3 (100 ng/ml) and IL-2 (100 U/ml). In both cases, dexamethasone at $10^{-7}$M (Sigma) plus Vitamin D3 at $2 \times 10^{-8}$M (BIOMOL Research Labs, Plymouth Meeting, Pa.) were added during the activation process.

Supernatants for analysis of cytokine production were harvested. After 7-day culture, mean cell recoveries from $1 \times 10^6$ cells from all treatment groups were not significantly different. Alternatively, immunofluorescence staining and flow cytometric analysis were used to assess IL-2 and IFN-γ producing cells. Reagents for this were purchased from PharMingen and used according to the manufacturer's instructions. Briefly, Cytofix/Cytoperm Plus (with GolgiStop) containing monensin was added to the above cultures for the final 16 h of culture to block intracellular transport processes. An ultrasensitive IL-4 ELISA was purchased from BioSource Europe (Wafford, GB) and had a lower limit of detection of 0.8 pg/ml IL-4. Other cytokines were measured using commercially available matched antibody pairs and following manufacturers instructions. IFN-γ antibody pairs were purchased from R&D Systems; IL-10 and IL-5 from PharMingen (Abingdon, GB). The lower limit of detection of the ELISA to IFN-γ was about 50 pg/ml, IL-5 about 200 pg/ml, and IL-10 about 50 pg/ml.

IV. Suppression In Vivo

An appropriate target for suppression is selected. For example, animal models exist of inflammatory of autoimmune pathologies which will be subject to suppression.

In one EAE model for multiple sclerosis, SJL/J and CSJLF1/J mice were obtained from The Jackson Laboratory. See, e.g., Cua, et al. (1999) J. Exp. Med. 189:1005–1010. BALB/cAnN mice were obtained from Taconic Farms, Inc.

Induction of EAE

Mouse spinal cord homogenate (MSCH) was prepared from 8–12-wk-old BALB/cAnN mice. Bovine MBP was obtained from Sigma Chemical Co. For active induction of EAE, mice were immunized intradermally with 2.5 mg of MSCH and 200 μg of Mycobacterium tuberculosis (strain H37RA; Difco) at days 0 and 7. Mice were examined and scored for clinical signs of EAE, and routine histopathological analyses of hematoxylin and eosin- or Luxol fast blue-stained paraffin sections were performed in a masked fashion.

T regulatory cells specific for selected antigen, e.g., OVA, and generated using the described method of VitD3/Dex culture were injected into mice on day minus 3. On day minus 4 mice had been injected intracranially with OVA (10 μg) plus alum (10 μl). The mice were injected with spinal cord homogenate in CFA at day 0 and at day 7 (and in many cases together with pertussis toxin). Mice were scored for pathology of EAE symptoms.

Suppression of pathology can be evaluated, as appropriate.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A method of obtaining a regulatory T cell, comprising contacting a naive CD4$^+$ T cell with a stimulatory signal and an appropriate amount of a combination of Vitamin D3 and Dexamethasone, wherein the stimulatory signal is a combination of an anti-CD3 antibody and an anti-CD28 antibody, and the regulatory T cell produces
   a) at least 100 ng of IL-10 per $10^6$ cells and
   b) less than 1 ng of IL-4 per $10^6$ cells and
   c) less than 30 pg of IL-5 per $10^6$ cells and/or
   d) less than 30 pg of IFN-γ per $10^6$ cells.

2. The method of claim 1, wherein:
   a) the regulatory T cell suppresses a response to a defined antigen; or
   b) the naive CD4$^+$ T cell is also contacted with a neutralizing antibody of:
      i) IL-4;
      ii) IFN-γ; and/or
      iii) IL-12.

3. The method of claim 1, wherein the contacting is in vitro.

4. The method of claim 3, wherein the contacting occurs two times.

5. The method of claim 3, wherein the amount of Vitamin D3 is about 4 times higher than the amount of Dexamethasone.

6. The method of claim 3, wherein the amount of:
   a) Vitamin D3 is at least $1 \times 10^{-8}$ M; and/or
   b) Dexamethasone is at least $2.5 \times 10^{-9}$ M.

7. The method of claim 6, wherein the amount of:
   a) Vitamin D3 is at least $3 \times 10^{-8}$ M; and/or
   b) Dexamethasone is at least $7.5 \times 10^{-9}$ M.

8. The method of claim 2; wherein:
   a) the response is a pathology inducing response; or
   b) the contacting occurs in the presence of at least two of the neutralizing antibodies.

9. A population of cells made by the method of claim 1.

* * * * *